United States Patent [19]

McKellin et al.

[11] 4,115,455
[45] Sep. 19, 1978

[54] REDUCTION OF CARBONYL-CONTAINING DIALKYL PEROXIDES TO HYDROXY-CONTAINING DIALKYL PEROXIDES

[75] Inventors: Wilbur H. McKellin, Deerfield, Ill.; William A. Swarts, Dover, N.J.

[73] Assignee: Pennwalt Corporation, Philadelphia, Pa.

[21] Appl. No.: 723,415

[22] Filed: Sep. 15, 1976

[51] Int. Cl.² .......................................... C07C 179/06
[52] U.S. Cl. .............................. 260/610 R; 260/610 B
[58] Field of Search ......................... 260/610 R, 610 B

[56] References Cited

U.S. PATENT DOCUMENTS

| 2,605,291 | 7/1952 | Barusch et al. | 260/610 R |
| 3,345,404 | 10/1967 | Schuller et al. | 260/514.5 |

OTHER PUBLICATIONS

Richardson et al., "J. Organic Chemistry" vol. 38, No. 25.
Milas JACS vol. 68, pp. 205–208 (1946).

*Primary Examiner*—Bernard Helfin
*Assistant Examiner*—Werren B. Lone

[57] ABSTRACT

A method of producing hydroxy-containing dialkyl peroxides of the formula

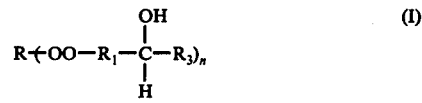

by either heterogeneously catalytically reducing or homogeneously, non catalytically chemically reducing carbonyl-containing dialkyl peroxides of the formula

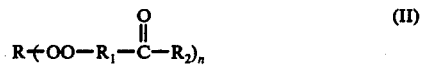

R, $R_1$, $R_2$ and $R_3$ are aliphatics. This invention also concerns novel hydroxy-containing dialkyl peroxide compounds having the structure of formula I.

13 Claims, No Drawings

REDUCTION OF CARBONYL-CONTAINING DIALKYL PEROXIDES TO HYDROXY-CONTAINING DIALKYL PEROXIDES

FIELD OF THE INVENTION

This invention relates to a method of producing hydroxy-containing dialkyl peroxides by reducing carbonyl-containing dialkyl peroxides. The carbonyl-containing dialkyl peroxides can be reduced to the hydroxy containing dialkyl peroxides by both homogenous, non-catalytic chemical reduction (hereinafter called chemical reduction), e.g. with lithium aluminum hydride, and heterogenous catalytic reduction (hereinafter called catalytic reduction), e.g., hydrogen and platinum metal.

STATE OF THE PRIOR ART

The following list of references shows the state of the prior art:
1. (a) U.S. Pat. No. 3,236,872
   (b) British Pat. No. 1,024,811
   (c) Canadian Pat. No. 757,653
   (d) Belgian Pat. No. 627,014
2. (a) M. R. Barush and J. Q. Payne, *J. Am. Chem. Soc.*, 75, 1987 (1953)
   (b) U.S. Pat. No. 2,605,291
3. J. Cartlidge and C. F. H. Tipper, *Anal. Chem. Acta.*, 22, 106–110 (1960); C.A. 54, 10631a (1960).
4. U.S. Pat. No. 3,345,404
5. N. S. Milas and D. M. Surgenor, *J. Am. Chem. Soc.*, 68, 205 (1946).
6. E. G. E. Hawkins, "Organic Peroxides", E. and F. F. Spon Ltd., London, 1961.
7. F. H. Dickey, et. al., *Ind. Eng. Chem.*, 41, 1673 (1949).
8. U.S. Pat. No. 2,403,771.
9. J. Mitchell Jr. and D. M. Smith, "Aquametry", Interscience, New York, 1948.
10. British Pat. No. 767,615.
11. H. Adkins and R. Conner, *J. Am. Chem. Soc.*, 53, 1091 (1931).
12. A. A. Balandin, Russian Chem. Revs., 33, No. 5, 258 (1964) English Translation.
13. W. H. Richardson, et. al., *J. Org. Chem.* 38, 4219–4225 (1973).
14. G. S. Akimova & M. P. Grimblat, *Zh. Obshch. Khim*, 1973, 43(5), 1199 (Russ); C.A. 79, 53433 (1973).

Catalytic reduction of dialkyl peroxides is known to cleave the oxygen-oxygen bond (references 4, 5 and 12). Numerous references can be found in Hawkin's book on Organic Peroxides (reference 6) showing that chemical reductions have been used for the quantitative determination of dialkyl peroxides (references 7, 8 and 9) indicating that cleavage of the peroxy oxygen-oxygen bond occurs readily. No cleaveage occurs in the catalytic reduction of the instant invention.

The catalytic reduction of primary- and secondary allylic tertiary-alkyl (aralkyl) peroxides to primary- and secondary-alkyl tertiary-alkyl (aralkyl) peroxides has been reported (reference 10):

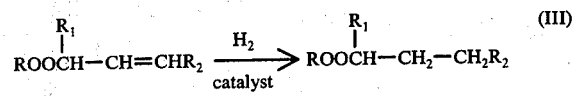

where: R is t-alkyl or t-aralkyl and $R_1$ and $R_2$ are hydrogen or lower alkyl of 1 to 5 carbons. The structure III compounds differ from the structure 1 compounds of the present disclosure in two ways:
1. They do not contain a hydroxyl group, and
2. They are not di-tertiary-alkyl peroxides.

Moreover, olefins are reduced much easier than carbonyl functions. Thus, it is not too surprising to catalytically reduce a carbon-carbon double bond while keeping the peroxy oxygen-oxygen bond intact especially in view of reference (5) which states that di-tertiary butyl peroxide "is unaffected by catalytic hydrogenation at room temperature using platinum oxide catalyst". These conditions will readily reduce a carbon-carbon double bond. However, carbonyl functions are more difficult to reduce to alcohol functions. For example, Adkin and Connor (Reference (11)) used hydrogen pressures of 1470 to 2205 psig at temperatures of 150° to 180° C. and a copper chromite catalyst (reported to be better than nickel catalysts) to reduce such carbonyl compounds as acetone, pinacolone, benzaldehyde, furfural, 2-methyl-pentanone-4, and various others to the corresponding hydroxy compounds. Thus, it was not obvious from the prior art that carbonyl-containing dialkyl peroxides could be reduced to hydroxy-containing dialkyl peroxides. In fact, reference (12) predicts that the peroxy oxygen-oxygen bond should be cleaved before the carbonyl function is reduced in catalytic hydrogenations.

References 1, 2, 3, 13 and 14 teach the prior art hydroxy-containing peroxide compounds which are not within the scope of the instant invention. The main difference between the prior art compounds and the compounds of the instant invention is that the prior art compounds are non-cyclic mono-peroxides whereas the novel compounds of this invention are diperoxides or cyclic mono-peroxides.

SUMMARY OF THE INVENTION

This invention concerns:

A. A process for reducing carbonyl-containing dialkyl peroxides of the formula

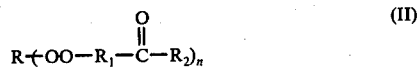

to the corresponding hydroxy-containing dialkyl peroxides

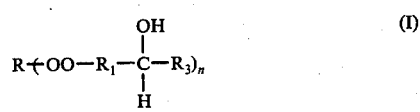

which comprises reacting II with a member selected from the group consisting of (A) hydrogen gas in the presence of a promoter and a catalyst selected from the group consisting of (i) platinum, palladium, rhodium or ruthenium on a carrier, (ii) platinum oxide and (iii) Raney nickel and (B) a chemical reducing agent preferably selected from the group consisting of an alkali metal aluminum hydride and an alkali metal borohydride, wherein:

a. R is a tertiary aliphatic radical of 4–15 carbons or a ditertiary aliphatic diradical of 8–30 carbons or a tri-tertiary aliphatic triradical of 10–21 carbons;

b. $R_1$ is a tertiary aliphatic or cycloaliphatic diradical of 3–15 carbons having the tertiary carbon attached to the peroxy oxygen;

c. $R_2$ and $R_3$ are selected from $-R_1-OO-R$, an aliphatic radical of 1–15 carbons, a cycloaliphatic radical of 3–15 carbons, and hydrogen, $R_2$ can also be a hydroxyl or lower alkoxy of 1 to 5 carbons;

d. $R_1$ can be linked with $R_2$ or $R_3$ to form a cycloaliphatic triradical of 3–10 carbons;

e. $n$ is an integer of 1, 2 or 3;

f. $R_2$ and $R_3$ can also be $R_1$ when $n$ is 2;

g. R can be linked to $R_1$ to form an aliphatic triradical of 6–20 carbons when $n$ is 1; and h. R can be linked to $R_2$ or $R_3$ to form an aliphatic diradical of 3–10 carbons when $n$ is 1.

B. Hydroxy-containing dialkyl peroxides of formula

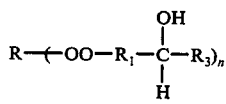

wherein:

a. R is selected from the group consisting of a tertiary alkyl radical of 4–10 carbons, a ditertiary alkylene diradical of 8–20 carbons, a ditertiary alkynylene diradical of 8–20 carbons, a tertiary bicycloalkyl radical of 8–10 carbons, a tertiary cycloalkyl radical of 6–8 carbons, a tertiary aralkyl radical of 9–12 carbons, a ditertiary aralkylene diradical of 12–18 carbons, a tri-tertiary-alkyl triradical of 10–21 carbons, a tri-tertiary-aralkyl triradical of 15–21 carbons, or a di or tri-radical containing a a combination of tertiary-alkyl, tertiary-cycloalkyl, tertiary-bicycloalkyl, and tertiary-aralkyl radicals of 8 to 21 carbons;

b. $R_1$ is a tertiary alkyl or cycloalkyl diradical of 3–15 carbons having a tertiary carbon attached to the peroxy oxygen;

c. $R_3$ is $-R_1OOR$ when $n$ is 1; $R_3$ is selected from the group consisting of hydrogen, alkyl of 1–15 carbons and cycloalkyl of 3–15 carbons and $R_3$ can be $R_1$ when $n$ is 2.

d. $n$ is 1, 2 or 3;

e. $R_1$ can be linked with $R_3$ to form an aliphatic triradical of 3 to 10 carbons;

f. R can be linked with $R_1$ to form an aliphatic triradical of 6 to 20 carbons when $n$ is 1;

g. R can be linked to $R_3$ to form an aliphatic diradical of 3 to 10 carbons when $n$ is 1.

DETAILED DESCRIPTION OF INVENTION

It has now been discovered that carbonyl-containing dialkyl peroxides of structure II can be both chemically and catalytically reduced to hydroxy-containing dialkyl peroxides of structure I. Note that the chemical reduction is a homogeneous non-catalytic reduction system; the catalytic reduction is a heterogeneous catalytic reduction system wherein the catalyst is insoluble in the system. Hydroxy-containing dialkyl peroxides of structure I are useful as free-radical generating catalysts for such applications as initiating vinyl monomer polymerizations, curing resins, crosslinking polymers, and in organic syntheses. Moreover, the structure I compounds are especially useful as dual purpose free radical generators wherein the hydroxy group is used as a handle for other chemical reactions and applications. For example, the hydroxyl group can be reacted with phosgene to obtain a dialkyl peroxide containing an acylating function (chloroformate group) which can subsequently be used to attach dialkyl peroxides to suitable substrates e.g. polymers containing reactive groups (e.g. hydroxy, amino, thiol, etc). Such peroxy-containing polymers are useful for preparing block and graft copolymers.

Hydroxy-containing dialkyl peroxides of structure I can also be reacted with the peroxides containing acylating functions to obtain dual temperature or sequential free radical generators. They can also be reacted with a variety of chemical reagents known to react with hydroxyl groups (e.g. acid chlorides, acid anhydrides, chloroformates, isocyanates, etc.) to obtain dialkyl peroxides of differing solubilities, volatility, melting points, stabilities, etc. Some of these reagents may possess additional groups which can import desirable properties in polymers such as: antistatic, dyeability, color, conductivity, stability, platability, adhesion, etc.

The definitions of R, $R_1$, $R_2$ and $R_3$ are structures I and II of the novel reduction processes are as follow:

R is (i) a tertiary aliphatic radical of 4–15 carbons, preferably a tertiary alkyl radical of 4–10 carbons, a tertiary bicycloalkyl radical of 8–10 carbons, a tertiary cycloalkyl radical of 6–10 carbons or a tertiary aralkyl radical of 9–12 carbons, (ii) a ditertiary aliphatic diradical of 8–30 carbons with the preferred diradical being a ditertiary alkylene diradical of 8–20 carbons, a ditertiary alkynylene diradical of 8–20 carbons, or a dietertiary aralkylene diradical of 12–18 carbons, (iii) a tri-tertiary aliphatic triradical of 10–21 carbons, preferably a tri-tertiary alkyl triradical of 10–21 carbons or a tri-tertiary-aralkyl triradical of 15–21 carbons, or (iv) a di- or tri-radical containing any combination of tertiary alkyl, tertiary aralkyl, tertiary cycloalkyl, or tertiary bicycloalkyl radicals.

$R_1$ is a tertiary aliphatic or cycloaliphatic diradical of 3–15 carbons having the tertiary carbon attached to the peroxy oxygen; the preferred diradicals for $R_1$ are tertiary alkyl or cycloalkyl diradicals of 3–15 carbons.

$R_2$ and $R_3$ are selected from (i) $-R_1-OO-R$, (ii) an aliphatic radical of 1–15 carbons with the preferred radicals being alkyl radicals of 1–15 carbons, (iii) a cycloaliphatic radical of 3–15 carbons with the preferred being cycloalkyl radicals of 3–15 carbons, or (iv) hydrogen; $R_2$ can also be selected from a hydroxyl or lower alkoxy of 1 to 5 carbons.

$R_1$ can be linked with $R_2$ or $R_3$ to form an aliphatic triradical preferably an alkyl triradical.

$n$ is an integer of 1, 2 or 3. When $n$ is 2, $R_2$ and $R_3$ can be equivalent to $R_1$.

R can be linked with $R_1$ to form an aliphatic triradical, preferably an alkyl triradical.

R can be linked with $R_2$ or $R_3$ to form an aliphatic diradical, preferably an alkyl diradical.

In the formula I for the novel hydroxy-containing dialkyl peroxide compounds the R, $R_1$ and $R_3$ radicals are defined as follow:

R is selected from the group consisting of a tertiary alkyl radical of 4–10 carbons, a ditertiary alkylene diradical of 8–20 carbons, a ditertiary alkynylene diradical of 8–20 carbons, a tertiary bicycloalkyl radical of 8–10 carbons, a tertiary cycloalkyl radical of 6–8 carbons, a tertiary aralkyl radical of 9–12 carbons, a ditertiary aralkylene diradical of 12–18 carbons, a tri-tertiary alkyl triradical of 10–21 carbons, a tri-tertiary-aralkyl triradical of 15–21 carbons, or a di- or tri-radical containing a combination of tertiary-alkyl, tertiary-aralkyl, tertiary-cycloalkyl, and tertiary-bicycloalkyl radicals of 8–21 carbons.

$R_1$ is a tertiary aliphatic or cycloaliphatic diradical of 3-15 carbons having the tertiary carbon attached to the peroxy oxygen; the preferred diradicals for $R_1$ are tertiary alkyl or cycloalkyl diradicals of 3-15 carbons.

When $n$ is 1, $R_3$ is $-R_1-OO-R$. When $n$ is 2 or 3, $R_3$ is selected from the group consisting of hydrogen, alkyl radical of 1-15 carbons and cycloalkyl radical of 3-15 carbons and when $n$ is 2, $R_3$ can also be equivalent to $R_1$.

$R_1$ and $R_3$ can join to form an aliphatic triradical of 3-10 carbons, preferably an alkyl triradical of 3-10 carbons. $n$ is 1, 2 or 3.

R and $R_1$ can join to form an aliphatic triradical of 6-20 carbons, preferably an alkyl triradical of 6-20 carbons.

R and $R_3$ can join to form an aliphatic diradical of 3-10 carbons, preferably an alkyl diradical of 3-10 carbons.

It should be noted that R, $R_1$, $R_2$ and $R_3$ can be substituted with non-interfering substituents such as halogens (fluorine, chlorine, etc.), lower alkoxy (methoxy, ethoxy, etc.), amido (carbamoyl, diethylcarbamoyl, acetamido, etc.), t-alkylperoxy, aryl (phenyl, toluyl, xylyl, naphthyl, etc.) and other substituents that will not affect the process. in some cases, the substituents may also be reduced without effecting the overall process giving structure I compounds containing the reduced substituents of the starting structure II compounds. Such reducible substituents may be: cyano, nitro, azo, other peroxides structures, and the like.

CATALYTIC REDUCTION PROCESS

Catalysts used in the catalytic reductions of the structure II compounds are (1) platinum, palladium, rhodium or ruthenium on various carriers, such as activated carbon, alumina or silica, (2) platinum oxide and (3) Raney nickel. The preferred catalysts are platinum oxide, platinum on activated carbon, rhodium on alumina, rhodium on activated carbon, ruthenium on alumina and ruthenium on activated carbon. The most preferred catalysts are platinum oxide, platinum on activated carbon, rhodium on alumina and ruthenium on activated carbon. The concentration of the catalyst should be 0.5% to 30% with the carriers and 0.1% to 3% without the carriers. The preferred catalyst concentration ranges are 0.75% to 25% with the carriers and 0.20 to 2.0% without the carriers with the most preferred concentrations being 1% to 20% with carriers and 0.25% to 1.5% without the carriers.

The reaction conditions for the catalytic process are as follows:

A. The reaction temperature in the reactor can range from $-20°$ C to $100°$ C with the preferred range being $-10°$ C to $60°$ C and the most preferred temperature range being $0°$ C to $35°$ C.

B. The hydrogen gas pressure in the reactor can range from 0 psig to 2000 psig with the preferred pressure range being 15 psig to 1000 psig and the most preferred pressure being 40 psig to 500 psig.

C. The period of time for the reaction to go to substantial completion depends on many factors such as pressure, temperature, catalyst used, promoter used, solvent and concentration of catalyst. Generally, however, the reaction time period can vary from about 0.5 hour to about 24 hours.

D. The concentrations of the carbonyl containing dialkyl peroxides in the catalytic reduction reaction, based on the percent of solvent, should be in the range of from 1% to about 30% with the preferred range being 5% to 25% and the most preferred range being 9% to 20%.

E. Solvents for the catalytic hydrogenations are water or water-alcohol mixtures. In the latter case the alcohol (usually ethanol) can represent from 0 to 75% of the solvent mixture. The alcohol serves to aid the solubilizing of the peroxy compound in the hydrogenation thereby giving more initimate contact of the peroxy compound with the catalyst and hydrogen. Other water soluble organic solvents that are inert to the hydrogenation conditions can be used. The amount of solvent used is such that the peroxy compound is present in an amount ranging from 1% to 30% of the solvent present with 5% to 25% being the preferred and 9% to 20% being the most preferred.

F. The platinum metal catalysts are significantly more effective in the hydrogenation of the structure II compounds when they are promoted by either acid or base. Platinum on activated carbon, platinum oxide and palladium on activated carbon are promoted by strong mineral acids such as alkylsulfonic acid with the alkyl radical having 1-4 carbons, arylsulfonic acids with aryl radical having 6-12 carbons, cycloalkylsulfonic acids with the cycloalkyl radical having 6 to 12 carbons, perchloric acid, fluoroboric acid, hydrochloric acid and sulfuric acid; the preferred acid promoters are methylsulfonic acid, phenylsulfonic acid, cyclohexylsulfonic acid, perchloric acid, hydrochloric acid, sulfuric acid, and fluoroboric acid. Rhodium and ruthenium on an alumina or an activated carbon carrier are promoted by bases such as alkali and alkaline earth metal hydroxides, carbonates and bicarbonates with the preferred basic promoter being the alkali metal hydroxides and the most preferred being sodium hydroxide and potassium hydroxide. The concentration of the acids can range from about 0.5% to about 35% with the preferred concentration range of the acid being about 1% to about 25% and the most preferred range being about 5% to about 20%. The concentration of the bases can range from about 0.1% to 3.0% with the preferred concentration of the bases being 0.3% to 2.0% and the most preferred range being 0.4% to 1.0%.

CHEMICAL REDUCTION PROCESS

The chemical reductions of the structure II compounds to the structure I compounds can be carried out preferably using alkali metal aliuminum hydrides or alkali metal borohydrides as the chemical reducing agents. Other chemical reducing agents well known in the art may also be used without deparing from the spirit and scope of this invention. The reactions using the alkali metal aluminum hydride are generally carried out in ether solvents such as diethyl ether and tetrahydrofuran while the reactions using the alkali metal borohydrides are generally carried out in ethers, alcohols (such as methanol, ethanol or isopropanol), water or dilute alkali. The alcohol solvents are not suitable for the aluminum hydride reductions. The structure II compounds can be reduced by using 1 mole of the hydride to 0.5 to 4 moles of the peroxide; the preferred concentration of the reducing agent is 1 mole of the hydride to 1 to 4 moles of the peroxide with the most preferred concentration being 1 mole of hydride to 1 to 2 moles of the peroxide. Using more than one mole of hydride per mole of structure II compound is not necessary. Although large excesses of hydride are not detrimental, they should be destroyed during the isolation of the structure I compounds and thus unnecessarily impart extra work and cost to the process.

Other reaction conditions for the chemical reduction process are as follows:

A. The reaction temperatures can range from −20° C to 100° C with the preferred range being −10° C to 60° C and the most preferred range being 0° C to 35° C. Usually, the rate of addition of the reducing agent to the reaction zone is regulated to control the reaction temperature since most reductions are exothermic. Hence, the reaction times will vary depending upon the rate of addition, extent of external cooling, reaction temperature, the structure II compound used, the amount of hydride being used, concentration, etc. Normally, the reaction is completed after the additions are completed. Generally, the reactions are stirred for 1 to 2 hours additionally to insure a complete reaction. Normally the total reaction time will vary from about 0.5 hour to about 3 hours depending on the above-mentioned factors.

B. The pressure in the reaction zone is maintained at atmospheric pressure. No hydrogen gas is used in the chemical reduction process because the hydrides supply the hydrogen.

C. The structure II peroxide concentration range in the reaction zone, based on the percent of the solvent, is generally from 1% to 30% with the preferred concentration being 5% to 25% and the most preferred range being 5% to 15%. In other words the amount of solvent used in the hydride reductions is such that the structure II compounds amount to 1% to 30% of the solvent used, with the preferred range being 5% to 25% and the most preferred range being 5% to 15%.

STRUCTURE II COMPOUNDS

The carbonyl-containing dialkyl peroxides (structure II) can be prepared by the strong acid catalyzed addition of a tertiary hydroperoxide to an α, β unsaturated ketone. For example, 2-methyl-2-(t-amylperoxy)-4-pentanone can be prepared as follows:

A reaction mixture of 11.8 g (0.12 mole) of mesityl oxide, 30 g of Amberlyst 15 sulfonic acid type ion-exchange resin, and 15.6 g (0.15 mole) of 89% t-amyl hydroperoxide was stirred at 25°-30° C for 20 hours and at 40° C for 1 hour. Hexane was added and the ion-exchange resin separated by filtration. The filtrate was washed with sodium bisulfite solution and with water and the organic layer dried over anhydrous magnesium sulfate. The hexane solvent was removed under reduced pressure and the 11.7 g of recovered product identified by its infrared spectrum as the following structure:

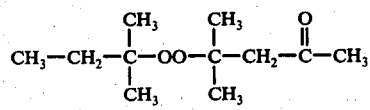

Another example of a method of preparing a structure II compounds is the method of preparing 2-methyl-2-(t-butylperoxy)-5-hexanone (Example II). This structure II ketone peroxide was prepared by the cuprous chloride catalyzed reaction of t-butyl hydroperoxide with methyl isoamyl ketone. The structure II precursor of Example X in the instant application is not a ketone peroxide. It is a carboxy-peroxide, i.e., $R_2$=OH. Such carboxy-peroxides can be prepared from ketone-peroxide (i.e., $R_2$=alkyl) by oxiding the ketone function to a carboxy function. The carboxy-peroxides can be esterified by conventional means to ester-peroxides, i.e., $R_2$=lower alkoxy. There are also several prior art patents that teach processes for preparing the structure II compounds: U.S. Pat. Nos. 3,842,129, 3,892,811, 3,755,454, 3,907,903 and Canadian Pat. No. 887,674.

The following compounds are a few of the many other structure II compounds that can be reduced to structure I compounds according to the present invention:

1. 4-(a,a-dimethylbenzylperoxy)-4-methyl-2-pentanone,
2. 4-[1,1,4-trimethyl-4-(t-butylperoxy)pentylperoxy]-4-methyl-2-pentanone,
3. 4-(1,1-dimethyl-3-hydroxybutylperoxy)-4-methyl-2-pentanone,
4. 1-(1-methylcyclohexylperoxy)-1-methyl-2-acetylcyclohexane,
5. 1-[3-(tert.-chlorobutylperoxy)-3-methylbutyryl]-4-chlorocyclohexane,
6. 1,4-di-[1-(1,1-dimethyl-2-acetylethylperoxy)-1-methylethyl]benzene,
7. 1-(tert.-butylperoxy)-1-(3-chloroacetonyl)cyclopentane,
8. 1,3,5-tri[1-(1,1-dimethyl-2-acetylethyl-peroxy)-1-methylethyl]benzene,
9. 1,2,4-tri[1-(1,1-dimethyl-2-acetyl-ethylperoxy)-1-methylethyl]benzene,
10. 3,3,7,7,10,10,13,13,-octamethyl-5-oxo-1,2,8,9-tetraoxacyclotridecane,
11. ethyl 3-(tert.-butylperoxy)-3-methylbutyrate,
12. 3-(tert.-butylperoxy)-3-methylbutyraldehyde,
13. methyl 3-(tert.-butylperoxy)-3-methyl-valerate,
14. ethyl 2-(tert.-butylperoxy)-2-methyl-propionate,
15. 3,3,7,7-tetramethyl-5-oxo-1,2-dioxacycloheptane, and
16. 3,3,6,6-tetramethyl-4-acetyl-1,2-dioxacyclohexane.

The following compounds are examples of structure (I) compounds:

1. 1,4-di-[1-(1,1-dimethyl-3-hydroxybutylperoxy)-1-methylethyl]benzene,
2. 1,3,5- and 1,2,4-tri[1-(1,1-dimethyl-3-hydroxybutylperoxy)-1-methylethyl]benzene,
3. 3,3,7,7,10,10,13,13-octamethyl-5-hydroxy-1,2,8,9-tetraoxacyclotridecane,
4. 3,3,7,7-tetramethyl-5-hydroxy-1,2-dioxacycloheptane, and
5. 3,3,6,6-tetramethyl-4-(1-hydroxyethyl)-1,2-dioxacyclohexane.

The following examples illustrate the subject invention but are not in limitation thereof:

EXAMPLE I

Preparation of 2-Methyl-2-(t-butylperoxy)-4-pentanol by Catalytic Hydrogenation

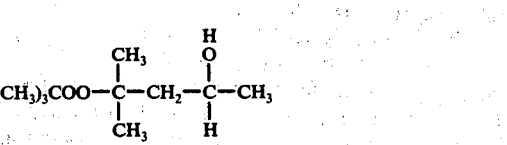

Structure I where R = $(CH_3)_3C—$; $R_1$ = $—\underset{\underset{CH_3}{|}}{\overset{\overset{CH_3}{|}}{C}}—CH_2—$;

and R$_3$ = CH$_3$—. n = 1.

A. Platinum Oxide Catalyst

A mixture containing 18.8 g (0.1 mole) of 2-methyl-2-(t-butylperoxy)-4-pentanone, 0.2 g of 82.9% platinum oxide,
25 ml of 2N hydrochloric acid solution and 75 ml. of ethanol was shaken in a Parr Hydrogenation apparatus under an initial pressure of hydrogen of 60 p.s.i.g. for 24 hours. The system was repressurized to 60 p.s.i.g. after the pressure had dropped to 55.5 p.s.i.g. After venting the hydrogen, the catalyst was removed by filtration, some of the alcohol solvent removed under reduced pressure and the mixture drowned into saturated ammonium sulfate solution. The organic layer was taken up in pentane, the pentane layer washed, dried over anhydrous sodium sulfate, and the pentane removed under reduced pressure.

The product weighed 12.9 g., and contained approximately 50% of 2-methyl-2-(t-butylperoxy)-4-pentanol as determined by chromatographic analysis.

B. Ruthenium Catalyst

A mixture of 18.8 g. (0.1 mole) of 2-methyl-2-(t-butylperoxy)-4-pentanone, 100 ml. of 0.1 N sodium hydroxide solution and 0.2 g. of commercial 5% ruthenium on carbon catalyst was shaken in a Parr Hydrogenation Apparatus at 25° C. for 20 hours, under a hydrogen pressure of 60 p.s.i.g. The organic layer was taken in pentane, the pentane solution washed with water, dried over anhydrous magnesium sulfate and the pentane removed under reduced pressure leaving 5.4 g. of product (28.7% recovery) which chromotographic analysis showed to contain 2-methyl-2-(t-butylperoxy)-4-pentanol.

C. Rhodium Catalyst

The above procedure was carried out using 1.0 g. of commercial 5% rhodium or alumina powder catalyst and 100 ml. of 0.25 N sodium hydroxide solution. The recovered product was shown by chromatographic analysis to contain 2-methyl-2-(t-butyl-peroxy)-4-pentanol.

EXAMPLE II

Preparation of 2-Methyl-2-(t-butylperoxy)-5-hexanol by Catalytic Hydrogenation

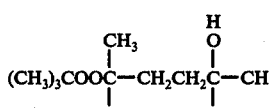

Structure I where R = (CH$_3$)$_3$C— ;

$R_1 = -\overset{CH_3}{\underset{CH_3}{C}}-CH_2CH_2-$ ; and R$_3$ = CH$_3$—. n = 1.

The catalytic hydrogenation of the carbonyl group in 2-methyl-2-(t-butylperoxy)-5-hexanone was carried out by shaking 5.0 g. (0.025 mole) of the ketone in a Parr Hydrogenation Apparatus with 25 ml. of 10% methanesulfonic acid solution and 1.0 g. of 5% platinum on carbon catalyst at 0° C. for 2 ½ hours with a hydrogen pressure of 60 p.s.i.g. At the end of the reaction time, the catalyst was separated by filtration, the product taken up in 50 ml. of pentane, the pentane solution washed to neutrality with water, dried over anhydrous magnesium sulfate and the pentane removed under reduced pressure. The recovered product weighed 3.3 g. (65% recovery). An infrared spectrum showed the presence of a hydroxyl band and the absorption band at 880 cm$^{-1}$ typical of the t-butylperoxy group.

EXAMPLE III

Preparation of 3,5,5-Trimethyl-3-(t-butylperoxy) cyclohexanol by Catalytic and Chemical Hydrogenations

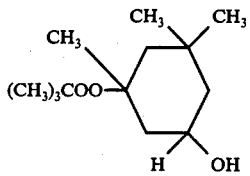

Structure I where R = (CH$_3$)$_3$C— ; and R$_1$ and R$_3$ together =

$-\overset{CH_3}{\underset{CH_2}{\overset{|}{C}}}-CH_2-\overset{CH_3}{\underset{CH_3}{\overset{|}{C}}}-CH_2-$ . n = 1.

A. Using Lithium Aluminumhydride

To a stirred solution of 3.08 g. (0.0815 mole) of lithium aluminumhydride dissolved in 250 ml. of ether, was added 22.8 g. (0.1 mole) of 3,5,5-trimethyl-3-(t-butylperoxy) cyclohexanone dissolved in 50 ml. of ether while the temperature was held at 5° C. When the addition was complete (40–50 minutes), the reaction mixture was stirred at 10° C. for 1 ½ hours. The unreacted hydride was used up by the additon of 35 ml. of wet ether followed by the dropwise addition of 50 ml. of water. The mixture was vigorously stirred while 15 g. of sodium tartrate and enough water was added to give a clear ether layer and a white aqueous layer. The ether layer was separated, washed with water to neutrality and dried over anhydrous magnesium sulfate. Evaporation of the ether gave 18.2 g. (79.3% recovery) of product showing a strong hydroxyl (—OH) band in the IR spectrum and the absence of carbonyl (—C═O) band. Iodometric assay showed the presence of active oxygen in the product. The IR band at 880 cm$^{-1}$, typical of the t-butylperoxy group, showed a strong absorption band.

B. Using Catalytic Hydrogenation

The catalytic hydrogenation of 3,5,5-trimethyl-3-(t-butylperoxy)-cyclohexanone, 10.0 g. (0.045 mole), was carried out in a Parr Hydrogenation Apparatus using 1.0 g. 5% Platinum on carbon catalyst and in the presence of 50 ml. of 10% methanesulfonic acid solution. The hydrogenation at 60 p.s.i.g. hydrogen pressure was started at 0° C. and the temperature allowed to rise to 21° C. After 2 ½ hours, the reaction was stopped, the product taken up in ether, the etheral solution washed to neutrality with water, dried over anhydrous magnesium sulfate and the ether removed under reduced pressure. Examination of the IR spectrum of the product showed that some of the desired product had been obtained as evidenced by the hydroxyl absorption band while some unreduced carbonyl was still present. Further catalytic hydrogenation at 35° C. for 18 hours caused a further increase in hydroxyl absorption band and reduction of the carbonyl absorption band.

EXAMPLE IV

Preparation of 2,6-Dimethyl-2,6-bis(t-butylperoxy)-4-heptanol by Chemical Reduction

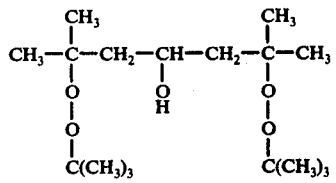

Structure I where R = $(CH_3)_3C-$ ; $R_1 = -\underset{\underset{CH_3}{|}}{\overset{\overset{CH_3}{|}}{C}}-CH_2-$ ; and $R_3 = (CH_3)_3COO-\underset{\underset{CH_3}{|}}{\overset{\overset{CH_3}{|}}{C}}-CH_2-$ . n = 1.

A solution of 5.32 g. (0.14 mole) of lithium aluminumhydride in 150 ml. of ether was prepared and stired at 10° C., while a solution of 22.25 g. (0.07 mole) of 2,6-dimethyl-2,6-bis(t-butylperoxy)-4-heptanone dissolved in 30 ml. of ether was added slowly over 30 minutes. The temperature was raised to 35° C. and the ethereal solution refluxed for 45 minutes. After cooling to 15° C., the excess lithium aluminumhydride was used up by the addition of wet ether to the reaction mixture, the precipitated salts dissolved by the addition of dilute hydrochloric acid, and the ether solution of the product separated, washed with water and dried oer anhydrous magnesium sulfate. The product was recovered by evaporation of the ether under reduced pressure. By active oxygen assay, the purity of the product was estimated at 91%.

EXAMPLE V

Preparation of 2-Methyl-2-(pinanylperoxy)-4-pentanol by Chemical Reduction

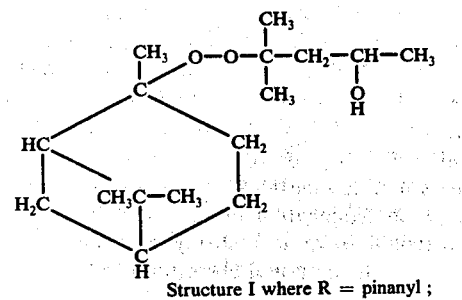

Structure I where R = pinanyl ;

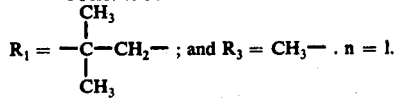

$R_1 = -\underset{\underset{CH_3}{|}}{\overset{\overset{CH_3}{|}}{C}}-CH_2-$ ; and $R_3 = CH_3-$ . n = 1.

A solution of 0.76 g. (0.02 mole) of lithium aluminumhydride dissolved in 75 ml. of ether was stirred at 10° C. while 5.36 g. (0.02 mole) of methyl-2-(pinanylperoxy)-4-pentanone dissolved in 10 ml. of ether was slowly added. After the addition was complete, the reaction mixture was stirred at 10°-15° C. for one hour longer. The excess lithium aluminumhydride was used up by adding 1.5 g. (0.02 mole) of ethyl acetate dissolved in 5 ml. of ether, followed by 20 ml. of wet ether and then 50 ml. of water and 5.0 g. of sodium tartrate. The mixture was stirred for 15 minutes, the aqueous layer separated and the ether layer washed with dilute hydrochloric acid solution and then with water. The aqueous alkaline layer was acidified with hydrochloric acid to dissolve the inorganic salts and the solution extracted with ether and the washed ether solution combined with the previous ether extract. The combined ether solution was dried over anhydrous magnesium sulfate and the ether removed under reduced pressure. The product, weighing 4.73 g. was obtained in 87.5% yield.

The IR spectrum of the product showed that its carbonyl absorption band had been eliminated and a strong hydroxyl band had been introduced. An iodometric test showed that active oxygen was present.

EXAMPLE VI

Preparation of 4,4,7,7,10,10,13,13-Octamethyl-2,15-Dihydroxy-5,6,11,12-tetraoxahexadecane by Chemical Reduction

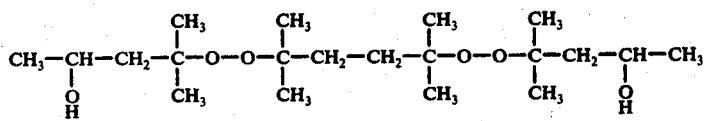

Structure I where R = $-\underset{\underset{CH_3}{|}}{\overset{\overset{CH_3}{|}}{C}}-CH_2-CH_2-\underset{\underset{CH_3}{|}}{\overset{\overset{CH_3}{|}}{C}}-$ ;

$R_1 = -\underset{\underset{CH_3}{|}}{\overset{\overset{CH_3}{|}}{C}}-CH_2-$ ; $R_3 = CH_3$; and n = 2.

Following the same general procedure as Example V, 7.46 g. (0.02 mole) of 4,4,7,7,10,10,13,13-octamethyl-2,15-dioxo-5,6,11,12-tetraoxahexadecane was reduced with 1.52 g. (0.04 mole) of lithium aluminumhydride dissolved in 100 ml. of ether. At the end of the reaction 3.0 g. of ethyl acetate was added to use up the excess hydride reagent. The product, weighing 6.78 g., was recovered in 90% yield.

EXAMPLE VII

Preparation of 4,4,7,7,10,10,13,13-Octamethyl-2,15-Dihydroxy-5,6,11,12-tetraoxa-8-hexadecyne by Chemical Reduction

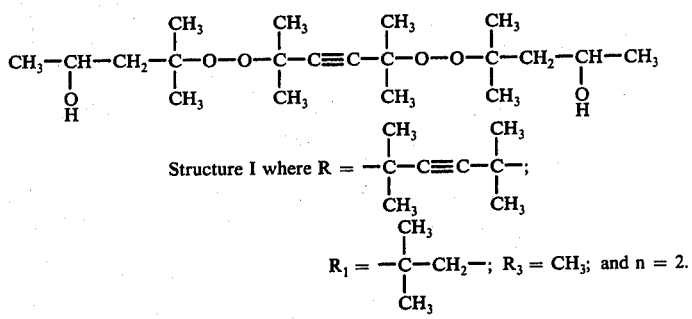

Following the same general procedure as Example V, 7.40 g. (0.02 mole) of 4,4,7,7,10,10,13,13-octamethyl-2,15-dioxo-5,6,11,12-tetraoxa-8-hexadecyne was reduced with 1.52 g. (0.04 mole) of lithium aluminumhydride dissolved in 100 ml. of ether.

The product, weighing 6.18 g., was recovered in 83.2% yield.

EXAMPLE IX

Preparation of 2-Methyl-2-(1,1,3,3-tetramethylbutylperoxy)-4-pentanol by Non-Heterogeneous Reduction

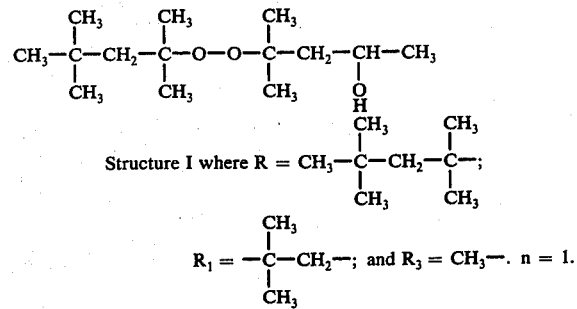

Following the same general procedure as Example V, 4.88 g. (0.02 mole) of 2-methyl-2-(1,1,3,3-tetramethylbutylperoxy)-4-pentanone was reduced with 0.76 g. (0.02 mole) of lithium aluminumhydride dissolved in 75 ml. of ether. The product, weighing 4.13 g., was recovered in 84% yield.

EXAMPLE X

Preparation of 3-Methyl-3-(t-butylperoxy)butanol-1 by Chemical Reduction

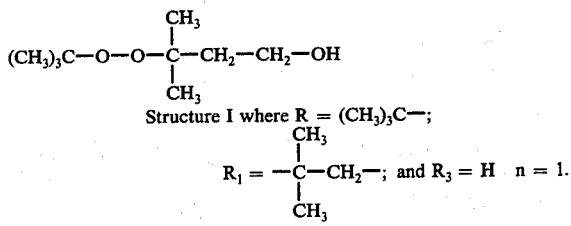

Following the same general procedure as Example V 3.80 g. (0.02 mole) of 3-methyl-3-(t-butylperoxy) butyric acid was reduced with 1.52 g. (0.04 mole) of lithium aluminumhydride dissolved in 75 ml. of ether. At the end of the reaction, 2.64 g. (0.03 mole) of ethyl acetate was added to use up the excess hydride reagent. The product, weighing 3.25 g., was recovered in 92.5% yield.

EXAMPLE XI

Curing an Unsaturated Polyester-Styrene Resin with the Hydroxy-Containing Dialkyl Peroxides of Structure I.

An unsaturated polyester resin was made by reacting maleic anhydride (1.0 mole), phthalic anhydride (1.0 mole), and propylene glycol (2.2 moles) until an acid number of 45–50 was obtained. To this was added hydroquinone at a 0.013% concentration. Seven parts of this polyester was diluted with 3 parts of styrene to obtain a homogeneous blend having a viscosity of 13.08 poise and a specific gravity of 1.14. To 20 gram samples of this blend was added the hydroxy-containing dialkyl peroxides of Examples III and IV in such amounts that the active oxygen content was equivalent to that obtained when the blend contained 1% t-butyl peroxybenzoate. The samples were placed in a constant temperature bath at 115° C. The internal temperature was recorded as a function to time to obtain the following results:

|  | EXAMPLE III PEROXIDE | EXAMPLE IV PEROXIDE |
| --- | --- | --- |
| Gel Time | 7.0 minutes | 4.2 minutes |
| Cure Time | 8.0 minutes | 5.6 minutes |
| Peak Exotherm | 450° F | 448° F |
| Barcol Hardness | 40 - 50 | 45 - 50 |

Without an initiator or curing agent, no cure of this resin blend occurred after more than 30 minutes at 115° C. Example XI illustrates that the hydroxy-containing dialkyl peroxides of structure I are useful for curing unsaturated polyestermonomer resins. Reference (1) discusses the utility of the structure I compound of Example I as a crosslinking agent for polyolefins and silicone rubbers. Thus, the structure I compounds are indeed generators of useful free radicals.

EXAMPLE XII (Sodium Borohydride Example)

2-Methyl-2-(t-butylperoxy)-4-pentanone (18.8 grams, 0.1 mole) was added dropwise to a stirred mixture of 50 grams of 0.2 N sodium hydroxide and 5.6 grams of sodium borohydride at 20°–25° C. There was a moderate exotherm during the addition. The reaction mixture was then stirred at 25°–30° C for 4 more hours and then acidified with hydrochloric acid to pH=2–3. The reaction mixture was extracted with diethyl ether. The ether layer was washed with water, 10% sodium bicarbonate until neutral, dried with magnesium sulfate, filtered, and the ether evaporated to leave 9.8 grams of product which were shown by gas chromatography to contain a substantial amount of 2-methyl-2-(t-butylperoxy)-4-hydroxypentane.

What is claimed is:

1. A process of reducing carbonyl-containing dialkyl peroxide of the formula $$R{+}OO{-}R_1{-}\overset{\overset{O}{\|}}{C}{-}R_2)_n \qquad (II)$$

to the corresponding hydroxy-containing dialkyl peroxide of the formula $$R{+}OO{-}R_1{-}\underset{\underset{H}{|}}{\overset{\overset{OH}{|}}{C}}{-}R_3)_n \qquad (I)$$

which comprises reacting II in the temperature range of −20° to 100° C and a pressure range of 0–200 psig with a member selected from the group consisting of (A) hydrogen gas in the presence of a promoter and a catalyst selected from the group consisting of (i) platinum, palladium, rhodium or ruthenium on a carrier, (ii) platinum oxide and (iii) Raney nickel wherein the concentration of said catalyst is in the range of 0.5–30% on the carrier and 0.1–3% without the carrier and (B) a hydride selected from the group consisting of an alkali metal aluminum hydride and an alkali metal borohydride wherein the hydride to peroxide ratio is in the range of 1 mole to 0.5–4 moles, wherein:

$n$ is 1 to 3 with provisos (a) through (n) below:

a. when $n$ is 1, R is selected from the group consisting of tertiary alkyl of 4–10 carbons, tertiary bicycloalkyl of 8–10 carbons, tertiary cycloalkyl of 6–10 carbons and tertiary aralkyl of 9 carbons;

b. when $n$ is 2, R is selected from the group consisting of ditertiary alkylene diradical of 8–20 carbons, ditertiary alkynylene diradical of 8–20 carbons, and ditertiary aralkylene diradical of 12 carbons;

c. when $n$ is 3, R is selected from the group consisting of tri-tertiary alkyl triradical of 10–21 carbons and tri-tertiary-aralkyl triradical of 15 carbons;

d. $R_1$ is a tertiary alkyl or cycloalkyl diradical of 3–15 carbons having the tertiary carbon attached to the peroxy oxygen;

e. $R_2$ and $R_3$ are selected from the group consisting of —$R_1$—OO—R, alkyl of 1–15 carbons, cycloalkyl of 3–15 carbons, and hydrogen; $R_2$ can also be selected from the group consisting of a hydroxyl and lower alkoxy of 1–5 carbons;

f. $R_1$ can be linked with $R_2$ or $R_3$ to form a cycloalkyl triradical of 3–10 carbons;

g. when $n$ is 1, R can be linked to $R_1$ to form an alkyl triradical of 6–20 carbons; and h. when $n$ is 1, R can be linked to $R_2$ or $R_3$ to form an alkyl diradical of 3–10 carbons.

2. The process of claim 1 wherein the reduction is performed with hydrogen gas in the presence of the promoter and catalyst.

3. The process of claim 2 wherein the catalyst is selected from platinum on activated carbon, platinum oxide and palladium on activated carbon, and the promoter is selected from an alkylsulfonic acid with the alkyl radical having 1–4 carbons, arylsulfonic acid with the aryl radical having 6–12 carbons, cycloalkylsulfonic acid with the cycloalkyl radical having 6–12 carbons, perchloric acid, fluoroboric acid, hydrochloric acid and sulfuric acid.

4. The process of claim 2 wherein the catalyst is selected from rhodium or ruthenium on an activated carbon or alumina carrier and the promoter is selected from an alkali metal hydroxide, an alkaline earth metal hydroxide, a carbonate and a bicarbonate.

5. The process of claim 2 wherein the reduction is performed in water containing from 0 to 75% of an organic alcohol inert to the hydrogenation conditions.

6. The process of claim 1 wherein the reduction is performed in the presence of lithium aluminumhydride in an organic ether solvent.

7. The process of claim 6 wherein the ratio of said hydride to (II) is about 1:0.5 to 4.

8. The process of claim 7 wherein the hydride is lithium aluminumhydride.

9. Hydroxy-containing dialkyl peroxide compound of the formula:

$$R{-}{+}OO{-}R_1{-}\underset{\underset{H}{|}}{\overset{\overset{OH}{|}}{C}}{-}R_3)_n$$

wherein:

$n$ is 1 to 3 with provisos (a) through (d) recited below, a. when $n$ is 1, R is selected from the group consisting of tertiary alkyl radical of 4–10 carbons, tertiary bicycloalkyl radical of 8–10 carbons, tertiary cycloalkyl radical of 6–8 carbons and tertiary aralkyl radical of 9 carbons and $R_3$ is selected from —$R_1$—OO—R; and $R_1$ and $R_3$ can join to form a cycloaliphatic triradical of 3–10 carbons;

b. when $n$ is 2, R is selected from the group consisting of ditertiary alkylene diradical of 8–20 carbons, ditertiary alkynylene diradical of 8–20 carbons and ditertiary aralkylene diradical of 12 carbons and $R_3$ is selected from the group consisting of hydrogen, alkyl of 1–15 carbons, cycloalkyl of 3–15 carbons;

c. when $n$ is 3, R is selected from the group consisting of tri-tertiaryalkyl triradical of 10–21 carbons and tri-tertiary-aralkyl triradical of 15 carbons and $R_3$ is selected from hydrogen, alkyl of 1–15 carbons, and cycloalkyl of 3–15 carbons; and d. $R_1$ is a tertiary alkyl or cycloalkyl diradical of 3–15 carbons having a tertiary carbon attached to the peroxy oxygen.

10. The hydroxy-containing dialkyl peroxide compound of claim 9 wherein the compound is 3,5,5-trimethyl-3-(t-butylperoxy)cyclohexanol.

11. The hydroxy-containing dialkyl peroxide compound of claim 9 wherein the compound is 2,6-dimethyl-2,6-bis(t-butylperoxy)-4-heptanol.

12. The hydroxy-containing dialkyl peroxide compound of claim 9 wherein the compound is 4,4,7,7,10,10,13,13-octamethyl-2,15-dihydroxy-5,6,11,12-tetraoxahexadecane.

13. The hydroxy-containing dialkyl peroxide compound of claim 9 wherein the compound is 4,4,7,7,10,10,13,13-octamethyl-2,15-dihydroxy-5,6,11,12-tetraoxa-8-hexadecyne.

* * * * *